(12) United States Patent
Hacker et al.

(10) Patent No.: US 7,060,657 B2
(45) Date of Patent: Jun. 13, 2006

(54) COMBINATIONS OF CYCLOHEXANEDIONE OXIME HERBICIDES AND SAFENERS

(75) Inventors: Erwin Hacker, Hochheim (DE); Hermann Bieringer, Eppstein (DE); Hans-Philipp Huff, Eppstein (DE)

(73) Assignee: Bayer CropScience GmbH, Frankfurt (DE)

( * ) Notice: Subject to any disclaimer, the term of this patent is extended or adjusted under 35 U.S.C. 154(b) by 97 days.

(21) Appl. No.: 10/621,236

(22) Filed: Jul. 16, 2003

(65) Prior Publication Data
US 2004/0018940 A1 Jan. 29, 2004

(30) Foreign Application Priority Data
Jul. 18, 2002 (EP) ................... 02016006

(51) Int. Cl.
*A01N 25/32* (2006.01)
*A01N 43/56* (2006.01)

(52) U.S. Cl. .................................. 504/106
(58) Field of Classification Search ................ 504/106, 504/280
See application file for complete search history.

(56) References Cited

U.S. PATENT DOCUMENTS

| | | | |
|---|---|---|---|
| 4,249,937 A | 2/1981 | Iwataki et al. |
| 4,422,864 A | 12/1983 | Becker et al. |
| 5,190,573 A | 3/1993 | Misslitz et al. |
| 5,703,008 A | 12/1997 | Rösch et al. |
| 6,124,240 A | 9/2000 | Bieringer et al. |

FOREIGN PATENT DOCUMENTS

| | | |
|---|---|---|
| EP | 0 070 370 | 1/1983 |
| EP | 0 071 707 A1 | 2/1983 |
| EP | 0 456 112 A1 | 11/1991 |
| GB | 2 090 246 | 7/1982 |
| JP | 52-95636 | 8/1977 |
| JP | 52-112945 | 9/1977 |
| WO | WO 99/08520 | 2/1999 |
| WO | WO 99/57982 | 11/1999 |

*Primary Examiner*—S. Mark Clardy
(74) *Attorney, Agent, or Firm*—Frommer Lawrence & Haug LLP

(57) ABSTRACT

A herbicide-safener combination, which comprises:
(A) one or more herbicidal cyclohexanedione oxime ("dims") or an agriculturally acceptable salt or metal complex thereof, selected from the group consisting of
(A1) alloxydim,
(A2) butroxydim,
(A3) clefoxydim also known as BAS 625H,
(A4) clethodim,
(A5) cycloxydim,
(A6) sethoxydim,
(A7) tepraloxydim, and
(A8) tralkoxydim. and
(B) an antidotally effective amount of one or more compounds of formula (I) or a salt thereof:

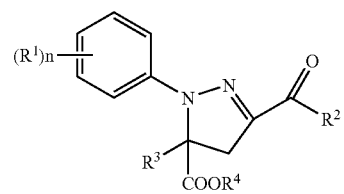

(I)

in which $R^1$, $R^2$, $R^3$, $R^4$ and n are as defined in the description, which is suitable for the selective control of harmful plants in crops of useful plants.

19 Claims, No Drawings

COMBINATIONS OF CYCLOHEXANEDIONE OXIME HERBICIDES AND SAFENERS

The invention relates to the technical field of herbicide-safener combinations and compositions for crop protection, in particular combinations of the cyclohexanedione oxime herbicides ("dims") and specific safeners which combinations are highly suitable for selective control of harmful plants in crops of useful plants.

Cyclohexanedione oxime herbicides ("dims") are a class of compounds which are known to be suitable for various herbicidal purposes. The herbicides include for example alloxydim, butroxydim, clefoxydim also known as BAS 625 H, clethodim, cycloxydim, sethoxydim, tepraloxydim and tralkoxydim each of which is known e.g. from the Pesticide Manual 12th edition (British Crop Protection Council); cf. JP 7795636, GB 2090246, EP 456112, U.S. Pat. No. 5,190,573, EP 70370, EP 71707, U.S. Pat. No. 4,422,864, JP 52112945 and U.S. Pat. No. 4,249,937.

Herbicidally active compounds of the cyclohexanedione oxime ("dims") type are generally used post-emergence for controlling grass weeds particularly in broad leaved crops or in some instances in rice, wheat or barley, and can be employed at relatively low application rates. However, these compounds are not always fully compatible with some important crop plants, such as soya bean, sunflower, cotton, flax, alfalfa, oilseed rape, tobacco, potatoes and sugar beet, or trees and vines, or the cereals wheat, barley, rice, maize (including transgenic selective herbicide tolerant varieties such as glufosinate tolerant varieties, for example ®Liberty link corn, or glyphosate tolerant varieties, for example ®Round-up-ready corn or soybean; or resistant mutants such as ALS herbicide resistant mutants e.g. mutants resistant to imidazolinones or sulfonylureas), so that their use as selective herbicides is in some instances limited. The herbicides can in this case only be used, if at all, at application rates which are compatible with the crops and so low that the desired broad herbicidal action against harmful plants is not ensured.

The injury to crop plants at herbicide application rates needed to control weed growth renders many herbicides unsuitable for control of a broad range of weed species in the presence of certain crops. The crop damage is made worse in cases where the weeds have become partly tolerant to herbicide treatments and thus require an increased application rate of herbicide to give acceptable control. Where weed growth in crops is uncontrolled however, this results in lower crop yield and reduced crop quality, as weeds will compete with crops for nutrients, light and water. It is already known that a reduction in herbicidal injury to crops without an unacceptable reduction in the herbicidal action can sometimes be accomplished by the use of crop protectants also referred to as "safeners", also sometimes referred to as "antidotes" or "antagonists". The safening effect generally depends on or is specific to the particular safener, the herbicidal partner and the crop where the active ingredients are applied.

It is generally known, for example from EP-A-0635996 (U.S. Pat. No. 5,703,008), that some safening effect may be obtained for certain pyrazoline safeners and cyclohexanedione oxime herbicides, however specific biological effects and specific herbicide-safener combinations have not been disclosed.

We have now found that, surprisingly, crop plants can be very effectively protected against undesirable damage by the group of cyclohexanedione oxime herbicides if the herbicides are applied together with certain compounds acting as safeners (herbicide antidotes) to the crop plants. Moreover the mixtures show an unexpectedly improved level of weed control compared to the effect of the cyclohexanedione oxime herbicides alone.

Accordingly, the present invention provides herbicide-safener combinations, for example in the form of preparations for use as herbicidal compositions, comprising:

(A) one or more herbicidal cyclohexanedione oximes ("dims") or an agriculturally acceptable salt or metal complex thereof, selected from the group consisting of:
(A1) alloxydim(methyl(E)-(RS)-3-[1-(alloxyimino)butyl]-4-hydroxy-6,6-dimethyl-2-oxocyclohex-3-enecarboxylate), or a salt or metal complex,
(A2) butroxydim(5-(3-butyryl-2,4,6-trimethylphenyl)-2-(1-ethoxyiminopropyl)-3-hydroxycyclohex-2-enone), or a salt or metal complex,
(A3) clefoxydim also known as BAS 625H (2-{1-[2-(4-chlorophenoxy)propoxyimino]butyl}-3-hydroxy-5-thian-3-ylcyclohex-2-enone), or a salt or metal complex,
(A4) clethodim((±)-2-[(E)-1-[(E)-3-chloroallyloxyimino]propyl]-5-[2-(ethylthio)propyl]-3-hydroxycyclohex-2-enone), or a salt or metal complex,
(A5) cycloxydim((±)-2-[1-(ethoxyimino)butyl]-3-hydroxy-5-thian-3-ylcyclohex-2-enone), or a salt or metal complex,
(A6) sethoxydim((±)-(EZ)-2-(1-ethoxyiminobutyl)-5-[2-(ethylthio)propyl]-3-hydroxycyclohex-2-enone), or a salt or metal complex,
(A7) tepraloxydim((EZ)-(RS)-2-{1-[(2E)-3-chloroallyloxyimino]propyl}-3-hydroxy-5-perhydropyran-4-ylcyclohex-2-en-1-one), or a salt or metal complex, and
(A8) tralkoxydim(2-[1-(ethoxyimino)propyl]-3-hydroxy-5-mesitylcyclohex-2-enone), or a salt or metal complex thereof, and
(B) an antidotally effective amount of one or more compounds of formula (I) or a salt thereof:

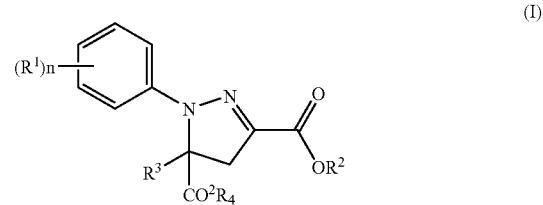

in which
$(R^1)_n$ is n radicals $R^1$ where the $R^1$ are identical or different and are each halogen or $(C_1-C_4)$-haloalkyl,
n is an integer from 1 to 3,
$R^2$ is hydrogen, $(C_1-C_6)$-alkyl, $(C_1-C_4)$-alkoxy-$(C_1-C_4)$-alkyl, $(C_3-C_6)$-cycloalkyl, tri-$(C_1-C_4)$-alkyl-silyl or tri-$(C_1-C_4)$-alkyl-silylmethyl,
$R^3$ is hydrogen, $(C_1-C_6)$-alkyl, $(C_1-C_6)$-haloalkyl, $(C_2-C_6)$-alkenyl, $(C_2-C_6)$-alkynyl or $(C_3-C_6)$-cycloalkyl, and
$R^4$ is hydrogen or $(C_1-C_{12})$-alkyl.

Preferably $(R^1)_n$ is n radicals $R^1$ where the $R^1$ are identical or different and are each F, Cl, Br or $CF_3$.
Preferably n is 2 or 3.
Preferably $R^2$ is hydrogen or $(C_1-C_4)$-alkyl.
Preferably $R^3$ is hydrogen, $(C_1-C_4)$-alkyl, $(C_2-C_4)$-alkenyl or $(C_2-C_4)$-alkynyl.
Preferably $R^4$ is hydrogen or $(C_1-C_8)$-alkyl.
More preferably $(R^1)_n$ is selected from the group consisting of 2,4-$Cl_2$, 2,4-$Br_2$, 2-$CF_3$-4-$Cl$ and 2-$Cl$-4-$CF_3$.

More preferably $R^2$ is hydrogen or $(C_1-C_4)$-alkyl.
More preferably $R^3$ is hydrogen or $(C_1-C_4)$-alkyl.
More preferably $R^4$ is hydrogen or $(C_1-C_4)$-alkyl.

A preferred class of safeners (B) for use in the present invention are of formula (I) wherein:
$(R^1)_n$ is n radicals $R^1$ where the $R^1$ are identical or different and are each F, Cl, Br or $CF_3$,
n is 2 or 3,
$R^2$ is hydrogen or $(C_1-C_4)$-alkyl,
$R^3$ is hydrogen, $(C_1-C_4)$-alkyl, $(C_2-C_4)$-alkenyl or $(C_2-C_4)$-alkynyl, and
$R^4$ is hydrogen or $(C_1-C_8)$-alkyl.

A more preferred class of safeners (B) for use in the present invention are of formula
(I) wherein:
$(R^1)_n$ is selected from the group consisting of 2,4-$Cl_2$, 2,4-$Br_2$, 2-$CF_3$-4-Cl and 2-Cl-4-$CF_3$,
$R^2$ is hydrogen or $(C_1-C_4)$-alkyl,
$R^3$ is hydrogen or $(C_1-C_4)$-alkyl, and
$R^4$ is hydrogen or $(C_1-C_4)$-alkyl.

Specific preferred safeners (B) of formula (I) are shown in Table 1 below:

TABLE 1

| Compound No. | $(R^1)_n$ | $R^2$ | $R^3$ | $R^4$ |
|---|---|---|---|---|
| (B1) | 2,4-$Cl_2$ | $C_2H_5$ | $CH_3$ | $C_2H_5$ |
| (B2) | 2,4-$Cl_2$ | $C_2H_5$ | $CH_3$ | $CH_3$ |
| (B3) | 2-$CF_3$-4-Cl | $C_2H_5$ | $CH_3$ | $C_2H_5$ |
| (B4) | 2,4-$Cl_2$ | $C_2H_5$ | $CH_3$ | n-$C_4H_9$ |
| (B5) | 2,4-$Cl_2$ | $C_2H_5$ | $CH_3$ | i-$C_4H_9$ |
| (B6) | 2,4-$Br_2$ | $C_2H_5$ | $CH_3$ | $C_2H_5$ |
| (B7) | 2-Cl-4-$CF_3$ | $C_2H_5$ | $CH_3$ | $CH_3$ |
| (B8) | 2-$CF_3$-4-Cl | $C_2H_5$ | $CH_3$ | $CH_3$ |
| (B9) | 2,4-$Br_2$ | $C_2H_5$ | $CH_3$ | $CH_3$ |
| (B10) | 2,4-$Cl_2$ | $C_2H_5$ | H | $CH_3$ |
| (B11) | 2,4-$Br_2$ | $C_2H_5$ | $CH_3$ | n-$C_4H_9$ |
| (B12) | 2,4-$Br_2$ | $C_2H_5$ | $CH_3$ | i-$C_4H_9$ |

Most preferably (B) is ethyl 1-(2,4-dichlorophenyl)-5-(ethoxycarbonyl)-5-methyl-2-pyrazoline-3-carboxylate (B1) ("Mefenpyr-diethyl", see "The Pesticide Manual", 12th edition 2000, pp. 594–595), as described in WO 91/07874.

The safeners (B) used in the combinations of the present invention are understood to embrace all stereoisomers and mixtures thereof, as well as their salts.

The advantageous safener effects are observed when the active compounds (A) and (B) are applied simultaneously, however, they can also frequently be observed when the active compounds are applied at different times (splitting). It is also possible to apply the active compounds in a plurality of portions (sequential application), for example after pre-emergence applications, followed by post-emergence applications or after early post-emergence applications, followed by medium or late post-emergence applications. It is also possible to use the safeners as a dressing for pre-treating the seeds of the crop plants or plant seedlings.

The active compounds of the combination in question are preferably supplied jointly or within a short interval.

The herbicide-safener combinations very effectively reduce or eliminate phytotoxic effects which can occur when the herbicidally active compounds (A) are used in useful plants. Additionally, the herbicidal activity against many harmful plants is surprisingly increased. The combinations permit a higher dosage (application rate) of the herbicide compared to the individual application of the herbicide in crops of useful plants, and thus a more effective control of the competing harmful plants. The higher efficacy permits the control of species which are as yet uncontrolled (gaps), an extension of the period of application and/or a reduction in the number of individual applications required and—as a result for the user—weed control systems which are more advantageous economically and ecologically.

It has hitherto not been known and is also surprising that the phytotoxicity of the cyclohexanedione oxime herbicides ("dims") (A) can be reduced very effectively or even eliminated with the aid of safeners (B). In general, the cyclohexanedione oxime herbicides ("dims") have a distinct chemical structure and activity profile which is different from that known of other classes of herbicidally active compounds. Thus, the effect of the safeners in combination with cyclohexanedione oxime herbicides ("dims") has not been demonstrated before and could not have been predicted by analogy with known herbicide-safener combinations.

Clethodim (A4), cycloxydim (A5) and tepraloxydim (A7) or salts or metal complexes thereof are preferred herbicides (A) for the herbicide-safener combinations.

The cyclohexanedione oxime herbicides ("dims") are generally known, and their preparation is described, for example, in the above mentioned publications, or can be carried out, for example by or analogously to the methods described in these publications.

For the preferred compounds, their preparation and general conditions for their use and in particular for specific example compounds, reference is made to the descriptions of the publications mentioned, and these descriptions are also part of the present invention.

The cyclohexanedione oxime herbicides ("dims") (A) may exist in enolic tautomeric forms that may give rise to geometric isomers around the enolic double bond. All such isomers and mixtures thereof are embraced by the present invention.

The cyclohexanedione oxime herbicides ("dims") (A) can form salts by replacing the hydrogen of the enol form of the dione, by an agriculturally suitable cation. These salts are, for example, metal salts, in particular alkali metal salts or alkaline earth metal salts, in particular sodium salts and potassium salts, or else ammonium salts, salts with organic amines or quaternary ammonium salts. The metal complexes can form when one or both of the oxygen atoms of the dione moiety act as chelating agents to a metal cation. Examples of such cations include zinc, manganese, cupric, cuprous, ferric, ferrous, titanium and aluminium.

The compounds of the formula (I) can form salts by addition of a suitable inorganic or organic acid, such as, for example, HCl, HBr, $H_2SO_4$ or $HNO_3$, but also oxalic acid or sulfonic acids, to a basic group, such as, for example, amino or alkylamino. Suitable substituents which are present in deprotonated form, such as, for example, sulfonic acids or carboxylic acids, can form inner salts with groups which for their part can be protonated, such as amino groups. Salts can also be formed by replacing the hydrogen of suitable substituents, such as, for example, sulfonic acids or carboxylic acids, by an agriculturally suitable cation. These salts are, for example, metal salts, in particular alkali metal salts or alkaline earth metal salts, in particular sodium salts and potassium salts, or else ammonium salts, salts with organic amines or quaternary ammonium salts.

In the formula (I) the radicals alkyl, alkoxy, haloalkyl and the corresponding unsaturated radicals can in each case be straight-chain or branched in the carbon skeleton. Unless specifically mentioned otherwise, the lower carbon skeletons, for example with 1 to 6 carbon atoms or in the case of unsaturated groups with 2 to 6 carbon atoms are preferred for these radicals. Alkyl radicals, also in the composed meanings, such as alkoxy, haloalkyl, and the like, are, for example, methyl, ethyl, n- or isopropyl, n-, i-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methyl-prop-2-en-1-yl, 2-methylprop-2-en-1-yl, but-2-en-1-yl, but-3-en-1-yl, 1methyl-but-3-en-1-yl and 1-methyl-but-2-en-1-yl; alkynyl is, for example, propargyl, but-2-yn-1-yl, but-3-yn-1-yl, 1-methylbut-3-yn-1-yl.

Cycloalkyl is a carbocyclic saturated ring system having preferably 3–8 carbon atoms, for example cyclopropyl, cyclobutyl, cyclopentyl or cyclohexyl.

Halogen is, for example, fluorine, chlorine, bromine or iodine. Haloalkyl is alkyl, alkenyl and alkynyl, respectively, which are partially or fully substituted by halogen, preferably by fluorine, chlorine and/or bromine, in particular by fluorine or chlorine, for example, monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$.

Preference is given to herbicide-safener combinations comprising a herbicidally effective amount of one or more compounds (A) and an antidotally effective amount of one or more compounds (B).

Preferred combinations include:
(A1)+(B1), (A2)+(B1), (A3)+(B1), (A4)+(B1), (A5)+(B1), (A6)+(B1), (A7)+(B1),
(A1)+(B2), (A2)+(B2), (A3)+(B2), (A4)+(B2), (A5)+(B2), (A6)+(B2), (A7)+(B2),
(A1)+(B3), (A2)+(B3), (A3)+(B3), (A4)+(B3), (A5)+(B3), (A6)+(B3), (A7)+(B3),
(A1)+(B4), (A2)+(B4), (A3)+(B4), (A4)+(B4), (A5)+(B4), (A6)+(B4), (A7)+(B4),
(A1)+(B5), (A2)+(B5), (A3)+(B5), (A4)+(B5), (A5)+(B5), (A6)+(B5), (A7)+(B5),
(A1)+(B6), (A2)+(B6), (A3)+(B6), (A4)+(B6), (A5)+(B6), (A6)+(B6), (A7)+(B6),
(A1)+(B7), (A2)+(B7), (A3)+(B7), (A4)+(B7), (A5)+(B7), (A6)+(B7), (A7)+(B7),
(A1)+(B8), (A2)+(B8), (A3)+(B8), (A4)+(B8), (A5)+(B8), (A6)+(B8), (A7)+(B8),
(A1)+(B9), (A2)+(B9), (A3)+(B9), (A4)+(B9), (A5)+(B9), (A6)+(B9), (A7)+(B9),
(A1)+(B10), (A2)+(B10), (A3)+(B10), (A4)+(B10), (A5)+(B10), (A6)+(B10), (A7)+(B10),
(A1)+(B11), (A2)+(B11), (A3)+(B11), (A4)+(B11), (A5)+(B11), (A6)+(B11), (A7) +(B11), and
(A1)+(B12), (A2)+(B12), (A3)+(B12), (A4)+(B12), (A5)+(B12), (A6)+(B12), (A7)+(B12).

More preferred combinations include:
(A4)+(B1), (A5)+(B1), (A7)+(B1),
(A4)+(B2), (A5)+(B2), (A7)+(B2),
(A4)+(B3), (A5)+(B3), (A7)+(B3),
(A4)+(B4), (A5)+(B4), (A7)+(B4),
(A4)+(B5), (A5)+(B5), (A7)+(B5),
(A4)+(B6), (A5)+(B6), (A7)+(B6),
(A4)+(B7), (A5)+(B7), (A7)+(B7),
(A4)+(B8), (A5)+(B8), (A7)+(B8),
(A4)+(B9), (A5)+(B9), (A7)+(B9),
(A4)+(B10), (A5)+(B10), (A7)+(B10),
(A4)+(B11), (A5)+(B11), (A7)+(B11), and
(A4)+(B12), (A5)+(B12), (A7)+(B12).

Surprisingly, it has been found that the herbicidal activity of the herbicide-safener combinations, for the control of certain weed species is greater than expected. While the safener has a negligible herbicidal effect when applied alone, the herbicidal effect of the combination with the herbicide is greater than that of the herbicide alone.

The combinations of the compounds (A) or their salts and the safeners (B) can be used, for example, as such or in the form of their preparations (formulations) combined with other pesticidally active substances, such as, for example, insecticides, acaricides, nematicides, herbicides, fungicides, safeners, fertilizers and/or growth regulators, for example in the form of a finished formulation or tank mixes. The preferred additional active compounds are herbicides.

Also preferred according to the invention are those combinations in which one or more further active compounds of a different structure [active compounds (C)] are added, such as:
(A1)+(B1)+(C), (A2)+(B1)+(C), (A3)+(B1)+(C), (A4)+(B1)+(C), (A5)+(B1)+(C), (A6)+(B1)+(C), (A7)+(B1)+(C), wherein (C) is one or more other active compounds.

Preferred combinations in which one or more further active compounds of a different structure [active compounds (C)] are added include:
(A4)+(B1)+(C), (A5)+(B1)+(C), (A7)+(B1)+(C).

Suitable active compounds (C) which can be combined with the active compounds according to the invention in mixed formulations or in a tank mix are, for example, known active compounds, preferably herbicides, as described, for example, in Weed Research 26, 441–445 (1986), or "The Pesticide Manual", 12th edition, The British Crop Protection Council and the Royal Soc. of Chemistry, 2000 and the literature cited therein, or the Compendium of Pesticide Common Names (available from the Internet). For example, the following active compounds may be mentioned as known herbicides or plant growth regulators and which can be combined with the compounds of the formula (A) and (B); hereinbelow, the compounds are either named by the "common name" (in most cases in English spelling) in accordance with the International Organization for Standardization (ISO) or by the chemical names, if appropriate together with a customary code number:

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; ametryn; amicarbazone, amidochlor, amidosulfuron; amitrol; AMS, i.e. ammonium sulfamate; anilofos; asulam; atrazin; azafenidin, azimsulfurone (DPX-A8947); aziprotryn; barban; BAS 516 H, i.e. 5-fluoro-2-phenyl-4H-3,1-benzoxazin-4-one; beflubutamid, benazolin(-ethyl); benfluralin; benfuresate; bensulfuron(-methyl); bensulide; bentazone(-sodium); benzobicyclon, benzofenap; benzofluor; benzoylprop(-ethyl); benzthiazuron; bialaphos (bilanafos); bifenox; bispyribac (-sodium), bromacil; bromobutide; bromofenoxim; bromoxynil; buminafos; busoxinone; butachlor; butafenacil, butamifos; butenachlor; buthidazole; butralin; butylate; cafenstrole (CH-900); carbetamide; carfentrazone(-ethyl); CDM, i.e. 2-chloro-N,N-di-2-propenylacetamide; CDEC, i.e. 2-chloroallyl diethyldithiocarbamate; chlomethoxyfen; chlorazifop-butyl, chloramben; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; cinidon(-methyl and -ethyl), cinmethylin; cinosulfuron; clodinafop and its ester derivatives (for example clodinafop-propargyl); clomazone; clomeprop; cloproxydim; clopyralid; clopyrasulfuron(-methyl), cloransulam(-methyl), cumyluron (JC 940); cyanazine; cycloate; cyclosulfamuron (AC 104); cycluron; cyhalofop and its ester derivatives (for example the butyl ester, DEH-112); cyperquat; cyprazine; cyprazole; daimuron; 2,4-D, 2,4-DB; 2,4-DB, dalapon; dazomet; desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr, dimefuron; dimepiperate, dimethachlor; dimethametryn; dimethenamid (SAN-582H); dimethenamid-P; dimethazone, dimethimipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e.

5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example the ethyl ester, HN-252); ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]phenyl]ethanesulfona mide; fenoprop; fenoxan, fenoxaprop and fenoxaprop-P and their esters, for example fenoxaprop-P-ethyl and fenoxaprop-ethyl; fentrazamide, fenuron; flamprop(-methyl or -isopropyl or -isopropyl-L); flazasulfuron; florasulam, fluazifop and fluazifop-P and their esters, for example fluazifop-butyl and fluazifop-P-butyl; fluazolate, flucarbazone(-sodium), fluchloralin; flufenacet (FOE 5043); flufenpyr; flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupropanate; flupyrsulfuron(-methyl or -sodium), flurenol(-butyl), fluridone; flurochloridone; fluroxypyr(-meptyl); flurprimidol, flurtamone; fluthiacet(-methyl), fluthiamide (flufenacet), fomesafen; foramsulfuron, fosamine; furilazole (MON 13900); furyloxyfen; glufosinate(-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; HC-252; hexazinone; imazamethabenz(-methyl); imazapyr; imazamethapyr, imazamox, imazapic, imazaquin and salts such as the ammonium salt; imazethamethapyr; imazethapyr; imazosulfuron; indanofan, iodosulfuron(-methyl-sodium), ioxynil; isocarbamid; isopropalin; isoproturon; isouron; isoxaben; isoxachlortole, isoxaflutole, isoxapyrifop; karbutilate; lactofen; lenacil; linuron; MCPA; MCPB; mecoprop; mefenacet; mefluidid; mesosulfuron(-methyl), mesotrione, metam; metamifop; metamitron; metazachlor; methabenzthiazuron; methazole; methoxyphenone; methyldymron; metobenzuron; metobromuron; S-metolachlor; (alpha-)metolachlor; metosulam (XRD 511); metoxuron; metribuzin; metsulfuron-methyl; MK-616; molinate; monalide; monocarbamide dihydrogensulfate; monolinuron; monuron; MT 128, i.e.

6-chloro-N-(3-chloro-2-propenyl)-5-methyl-N-phenyl-3-pyridazinamine; MT 5950, i.e. N-[3-chloro-4-(1-methyl-ethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron, oxaziclomefone, oxyfluorfen; paraquat; pebulate; pelargonic acid, pendimethalin; penoxulam; pentanochlor; pentoxazone, pethoxamid; perfluidone; phenisopham; phenmedipham; picloram; picolinafen, piperophos; piributicarb; pirifenop-butyl; pretilachlor; primisulfuron(-methyl); procarbazone-(sodium), procyazine; prodiamine; profluazole; profluralin; proglinazine(-ethyl); prometon; prometryn; propachlor; propanil; propaquizafop and its esters; propazine; propham; propisochlor; propoxycarbazone(-sodium), propyzamide; prosulfalin; prosulfocarb; prosulfuron (CGA-152005); prynachlor; pyraclonil; pyraflufen(-ethyl), pyrazolinate; pyrazon; pyrazosulfuron(-ethyl); pyrazoxyfen; pyribenzoxim, pyributicarb, pyridafol, pyridate; pyriftalid; pyrimidobac(-methyl), pyrithiobac(-sodium) (KIH-2031); pyroxofop and its esters (for example the propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione, sulfentrazone (FMC-97285, F-6285); sulfazuron; sulfometuron(-methyl); sulfosate (ICI-A0224); sulfosulfuron, TCA; tebutam (GCP-5544); tebuthiuron; terbacil; terbucarb; terbuchlor; terbumeton; terbuthylazine; terbutryn; TFH 450, i.e.

N,N-diethyl-3-[(2-ethyl-6-methylphenyl)-sulfonyl]-1H-1,2,4-triazole-1-carboxamide; thenylchlor (NSK-850); thiafluamide, thiazafluron; thiazopyr (Mon-13200); thidiazimin (SN-24085); thifensulfuron(-methyl); thiobencarb; tiocarbazil; tri-allate; triasulfuron; triaziflam, triazofenamide; tribenuron(-methyl); 2,3,6-trichlorobenzoic acid (2,3,6-TBA); triclopyr; tridiphane; trietazine; trifloxysulfuron(-sodium); trifluralin; triflusulfuron and its esters (for example the methyl ester, DPX-66037); trimeturon; tritosulfuron, tsitodef; vernolate; WL 110547, i.e. 5-phenoxy-1-[3-(trifluoromethyl)phenyl]-1H-tetrazole; BAY MKH 6561, UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

In individual cases, it may be advantageous to combine one of the compounds (A) with a plurality of compounds (B).

The application rate of the herbicides (A) can be varied within wide limits, the optimum amount depending on the herbicide in question, the spectrum of harmful plants and the crop plants. In general, the application rate is in the range from 0.001 g to 5 kg, preferably 10 g to 3 kg, very particularly 20 g to 2 kg of active compound (a.i.) per ha.

The herbicidally active compounds and the safeners can be applied together (as finished formulation or by the tank-mix method) or sequentially in any order. The weight ratio herbicide (A): safener (B) can vary within wide limits and is, for example, in the range from 1:200 to 200:1, preferably from 1:100 to 100:1, in particular from 1:50 to 50:1, most preferably from 1:20 to 20:1.

The level of herbicide dosage needed depends upon the particular weed infestation, weed spectrum to be controlled, formulation aids etc. Most preferred is the use of a relatively low dosage of the herbicide. The amounts of herbicidally active compound and safener which are optimal in each case depend on the active compound (A) and the safener (B) in question and on the type of crops to be treated, and they can be determined in each case by appropriate preliminary experiments.

Depending on their properties, the safeners may be used for pre-treating the seed of the crop plant (seed dressing) or the seedlings or be incorporated into the seed furrow prior to sowing. In the pretreatment of seedlings it is possible, for example, to spray the roots or the entire seedling with a solution of the safener or to dip them into such a solution. The use of one or more herbicides can then be carried out by the pre-emergence or post-emergence method.

Alternatively, it is possible to apply the safeners together with the herbicides, before or after emergence of the plants. Pre-emergence treatment includes both the treatment of the area under cultivation prior to sowing and the treatment of the areas under cultivation where the crops have been sown but not yet emerged. A sequential procedure, where the treatment with safener is carried out first followed, preferably closely, by application of the herbicide, is also possible. In individual cases, it may also be expedient to apply the safener after application of the herbicide.

In general, simultaneous application of safener and herbicide in the form of tank mixes or finished formulations is preferred.

The amount of safener used varies according to a number of parameters including the particular safener employed, the crop to be protected, the amount and rate of herbicide applied, the soil type and climatic conditions prevailing. Also, the selection of the specific safener for use in the method of the invention, the manner in which it is to be applied and the determination of the activity which is non-phytotoxic but antidotally effective, can be readily performed in accordance with common practice in the art. The application rate of safener can vary within wide limits and is generally in the range from 0.001 to 5 kg, preferably from 0.005 to 0.5 kg, of safener (a.i.) per hectare, or for seed treatment use is, for example, from 0.01 g to 10 g a.i. safener per kg seed, preferably 0.05 g to 5 g a.i. safener per kg seed, in particular 0.1 g to 3 g a.i. safener per kg seed.

If solutions of safeners are used in the seed treatment method wherein the seeds are soaked in the safener solution, the concentration of the safener in the solution is for example from 1 to 10000 ppm, preferably 100 to 1000 ppm based on weight.

Accordingly, the invention also provides a method for protecting crop plants against phytotoxic side effects of a herbicide (A), which method comprises the application of an amount, acting as an antidote, of one or more safeners (B) before, after or simultaneously with the herbicide (A) to the plants, parts of plants, plant seeds or the area under cultivation.

The herbicide-safener combinations according to the invention (i.e. the herbicidal compositions) have excellent herbicidal activity against a broad spectrum of economically important mono- and dicotyledonous harmful plants. The combinations also act efficiently on perennial weeds which produce shoots from rhizomes, root stocks or other perennial organs and which are difficult to control. The herbicidal effects of the combinations are similar to those of the herbicides (A) when used alone at comparable application rates.

If the combinations according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the combinations are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Specifically, some non-limiting representatives of the mono- and dicotyledonous weed flora which can be controlled by the combinations according to the invention may be mentioned by way of example.

Amongst the monocotyledonous weed species, those on which the active substances act efficiently are, for example, Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea and Cyperus species from the annual group and, amongst the perennial species, Agropyron, Cynodon, Imperata and Sorghum and also perennial Cyperus species.

In the case of dicotyledonous weed species, the spectrum of action extends to species such as, for example, Galium, Viola, Veronica, Lamium, Stellaria, Amaranthus, Sinapis, Ipomoea, Matricaria, Abutilon and Sida amongst the annuals and Convolvulus, Cirsium, Rumex and Artemisia in the case of the perennial weeds. Herbicidal action is also achieved in the case of dicotyledonous harmful plants such as Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica and Xanthium.

Harmful plants occurring under the specific cultivation conditions of rice, such as, for example, Sagittaria, Alisma, Eleocharis, Scirpus and Cyperus, are also outstandingly well controlled by the active substances according to the invention.

The herbicide-safener combinations (A)+(B) are suitable for weed control in a number of crop plants, for example in economically important crops such as the cereals wheat, barley, rice, maize and sorghum, or dicotyledonous crops, such as soya bean, sunflower and sugar cane, (including ®Liberty link corn and ®Round-up Ready corn or soybean, or mutant crops tolerant to ALS-inhibitors). Of particular interest is the use in cereals such as triticale, rye, rice, wheat (including durum wheat) and barley, including spring and winter varieties, and in particular wheat.

Owing to their herbicidal and plant growth-regulatory properties, the combinations can be employed for controlling harmful plants in known crops or in still to be developed genetically engineered plants, or mutant crops. Transgenic plants generally have particularly advantageous properties, for example resistance to certain pesticides, above all certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

The combinations according to the invention may also be employed in economically important transgenic crops of useful and ornamental plants, for example of cereals such as wheat, barley, rye, oats, millett, rice, manioc and maize or else in crops of sugar-beet, cotton, soya bean, oil seed rape, potatoes, tomatoes, peas and other vegetable species.

The invention also provides the use of the herbicidal compositions comprising combinations of (A)+(B) for controlling harmful plants, preferably in plant crops.

The active compound combinations according to the invention can be present both as mixed formulations of the two components, if appropriate with other active compounds, additives and/or customary formulation auxiliaries, which are then applied in a customary manner diluted with water, or be prepared as so-called tank mixes by joint dilution of the separately formulated or partially separately formulated components with water.

The compounds (A) and (B) or their combinations can be formulated in various ways depending on the prevailing biological and/or chemico-physical parameters. Examples of suitable formulation options are: wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dusts (DP), seed-dressing compositions, granules for broadcasting and soil application, or water-dispersible granules (WG), ULV formulations, micro-capsules or waxes.

The individual formulation types are known in principle and are described, for example, in Winnacker-Küchler, "Chemische Technologie" [Chemical Technology], Volume 7, C. Hauser Verlag Munich, 4th. Edition 1986; van Valkenburg, "Pesticides Formulations", Marcel Dekker, N.Y., 1973; K. Martens, "Spray Drying Handbook", 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxiaddukte" [Surface-active ethylene oxide adducts], Wiss. Verlagsgesellschoft, Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, such as other herbicides, fungicides or insecticides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic or nonionic type (wetting agents, dispersants), for example polyethoxylated alkyl phenols, polyethoxylated fatty alcohols, polyethoxylated fatty amines, alkanesulfonates, alkylbenzenesulfonates, sodium ligninsulfonate, sodium 2,2'-dinaphthylmethane-6,6'-disulfonate, sodium dibutylnaphthalene-sulfonate or else sodium oleoylmethyltaurinate.

Emulsifiable concentrates are prepared by dissolving the active compound in an organic solvent, for example butanol, cyclohexanone, dimethylformamide, xylene or else relatively high-boiling aromatic compounds or hydrocarbons with the addition of one or more surfactants of ionic or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitan esters.

Dusts are obtained by grinding the active compound with finely divided solid substances, for example talc, natural clays, such as kaolin, bentonite and pyrophyllite, or diatomaceous earth.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by processes such as spray-drying, fluidized-bed granulation, disk granulation, mixing using high-speed mixers, and extrusion without solid inert material.

The agrochemical formulations generally contain from 0.1 to 99% by weight, in particular from 2 to 95% by weight, of active compounds of types (A) and/or (B), the following concentrations being customary, depending on the type of formulations: In wettable powders the concentration of active compound is, for example, from about 10 to 95% by weight, the remainder to 100% by weight consisting of customary formulation constituents. In emulsifiable concentrates the concentration of active compound can be, for example, from 5 to 80% by weight.

Formulations in the form of dusts usually contain from 5 to 20% by weight of active compound, while sprayable solutions contain from about 0.2 to 25% by weight of active compound.

In the case of granules, such as dispersible granules, the content of active compound depends partly on whether the active compound is in liquid or solid form and on which granulation auxiliaries and fillers that are used. In water-dispersible granules the content is generally between 10 and 90% by weight.

In addition, said formulations of active compound may comprise the tackifiers, wetting agents, dispersants, emulsifiers, preservatives, antifreeze agents and solvents, fillers, colorants and carriers, antifoams, evaporation inhibitors, pH and viscosity regulators, thickeners and/or fertilizers which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions are conventionally not diluted any further with other inert substances prior to use.

The herbicidal compounds can be applied to the plants, parts of the plants, seeds of the plants or the area under cultivation (tilled soil), preferably to the green plants and parts of the plants and, if desired, additionally to the tilled soil.

A possible use is the joint application of the active compounds in the form of tank mixes, where the concentrated formulations of the individual active substances, in the form of their optimal formulations, are mixed jointly with water in the tank, and the resulting spray mixture is applied.

A joint herbicidal formulation of the combination according to the invention of the active compounds (A) and (B) has the advantage that it can be applied more easily because the amounts of the components have already been adjusted to one another in the correct ratio. Moreover, the auxiliaries of the formulation can be selected to suit each other in the best possible way, while a tank mix of various formulations may result in undesirable combinations of auxiliaries.

GENERAL FORMULATION EXAMPLES a) A dust is obtained by mixing 10 parts by weight of an active compound/active compound mixture and 90 parts by weight of talc as inert substance and comminuting the mixture in a hammer mill.

b) A wettable powder which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing
   75 parts by weight of an active compound/active compound mixture,
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disk mill and granulating the powder in a fluidized bed by spraying on water as granulation liquid.

f) Water-dispersible granules are also obtained by homogenizing and precomminuting, in a colloid mill,
   25 parts by weight of an active compound/active compound mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
subsequently grinding the mixture in a bead mill and atomizing and drying the resulting suspension in a spray tower by means of a single-substance nozzle.

BIOLOGICAL EXAMPLES

The following non-limiting Examples illustrate the invention.

Abbreviations used in the Tables below:

| | |
|---|---|
| TRZAW = | *Triticum aestivum* (winter wheat) |
| TRZDU = | *Triticum durum* desf. (durum wheat) |
| HORVS = | *Hordeum vulgare* (summer barley) |
| AVEFA = | *Avena fatua* |
| ALOMY = | *Alopecurus myosuroides* |
| PHAMI = | *Phalaris minor* |
| (A5) = | Cycloxydim |
| (A4) = | Clethodim |
| (A6) = | Sethoxydim |
| (A7) = | Tepraloxydim |
| (B1) = | Mefenpyr-diethyl |

The numbers in the columns refer to the percentage damage to the crop or weed.

Example 1

Post-Emergence Effect on Weeds and Selectivity in Winter Wheat (Field Trials)

Winter wheat was grown outdoors on plots under natural outdoor conditions, and seeds of typical harmful plants were laid out. Treatment with the herbicide (A), the safener (B) and the herbicide-safener combination (A)+(B) was carried out after the harmful plants had emerged and the wheat was in the growth stage between 3 and 5 leaves. The effect of the composition was assessed 28 days after treatment by scoring visually in comparison with untreated controls.

Table 2 shows that a good safening effect was obtained in the winter wheat, and in addition an excellent control of Phalaris minor and Alopecurus myosuroides (which were grown in a separate plot) was observed. The percentage control of the weed species are shown in comparison with the expected values given in parentheses.

TABLE 2

| Compound No. | Rate g a.i./ha | Phytotox (%) on TRZAW | Phytotox (%) on PHAMI | Phytotox (%) on ALOMY |
|---|---|---|---|---|
| A6 | 72 | 28 | 55 | 70 |
| B1 | 45 | 0 | 0 | 0 |
|  | 11 | 0 | 0 | 0 |
| A6 + B1 | 72 + 45 | 14 | 68 (55 + 0) | 75 (70 + 0) |
|  | 72 + 11 | 15 | 60 (55 + 0) | 83 (70 + 0) |

Example 2

Post-Emergence Effect on Weeds and Selectivity in Barley and Durum Wheat (Field Trials)

Field trials were carried out according to the above Example 1 but using the crops barley and durum wheat and applying a mixture of clethodim and mefenpyr-diethyl.

Table 3 shows that a good safening effect was obtained in barley and in durum wheat. Excellent control of weed species (which were grown in a separate plot), including typical cereal weed species, was observed.

TABLE 3

| Compound No. | Application rate (g ai/ha) | Phytotox (%) on HORVS | Phytotox (%) on TRZDU |
|---|---|---|---|
| (A4) | 7.5 | 51 | 32 |
|  | 15 | 67 | 56 |
| (B1) | 100 | 0 | 0 |
| (A4) + (B1) | 7.5 + 100 | 3 | 8 |
|  | 15 + 100 | 10 | 20 |

Example 3

Post-Emergence Effect on Weeds and Selectivity in Barley and Durum Wheat (Field Trials)

Field trials were carried out according to the above Example 2 and applying a mixture of clethodim and fenoxaprop-P-ethyl plus mefenpyr-diethyl.

Table 4 shows that a good safening effect was obtained in barley and in durum wheat. Excellent control of weed species (which were grown in a separate plot), including typical cereal weed species, was observed.

TABLE 4

| Compound No. | Application rate (g ai/ha) | Phytotox (%) on HORVS | Phytotox (%) on TRZDU |
|---|---|---|---|
| (A4) | 7.5 | 51 | 32 |
| (B1) | 100 | 0 | 0 |
| (B1) + fenoxaprop-P-ethyl | 25 + 92 | 18 | 8 |
| (A4) + (B1) + fenoxaprop-P-ethyl | 7.5 + 25 + 92 | 15 | 9 |

Example 4

Post-Emergence Effect on Weeds and Selectivity in Barley and Durum Wheat (Field Trials)

Field trials were carried out according to the above Example 2 and applying a mixture of tepraloxydim and mefenpyr-diethyl, or tepraloxydim and fenoxaprop-P-ethyl plus mefenpyr-diethyl.

Table 5 shows that a good safening effect was obtained in barley and in durum wheat using both mixtures.

Excellent control of weed species (which were grown in a separate plot), including typical cereal weed species, was observed.

TABLE 5

| Compound No. | Application rate (g ai/ha) | Phytotox (%) on HORVS | Phytotox (%) on TRZDU |
|---|---|---|---|
| (A7) | 8.25 | 78 | 70 |
| (B1) | 100 | 0 | 0 |
| (A7) + (B1) | 8.25 + 100 | 18 | 10 |
| (B1) + fenoxaprop-P-ethyl | 25 + 92 | 18 | 8 |
| (A7) + (B1) + fenoxaprop-P-ethyl | 8.25 + 25 + 92 | 17 | 16 |

Example 5

Post-Emergence Effect on Winter Wheat and Weeds (Field Trials)

Field trials were carried out according to the above Example 1 and applying a mixture of cycloxydim and fenoxaprop-P-ethyl+mefenpyr-diethyl to winter wheat and the weed Avena fatua at the 3–5 leaf growth stage. Assessment was 21 days after treatment.

Table 6 shows that a good safening effect was obtained in the winter wheat, and in addition an excellent control of Avena fatua (which was grown in a separate plot) was observed.

TABLE 6

| Compound No. | Rate g a.i./ha | Phytotox (%) on TRZAW | Phytotox (%) on AVEFA |
|---|---|---|---|
| A5 | 40 | 16 | 65 |
| B1 | 71 | 0 | 0 |
| A5 + B1 + fenoxaprop-P-ethyl | 40 + 71 + 16 | 8 | 99 |

What is claimed is:

1. A herbicide-safener combination, which comprises:
   (A) one or more herbicidal cyclohexanedione oximes or an agriculturally acceptable salt or metal complex thereof, selected from the group consisting of
   (A1) alloxydim,
   (A2) butroxydim,
   (A3) clefoxydim,
   (A4) clethodim,
   (A5) cycloxydim,
   (A6) sethoxydim,
   (A7) tepraloxydim, and
   (A8) tralkoxydim,
   and
   (B) an antidotally effective amount of one or more compounds of formula (I) or a salt thereof:

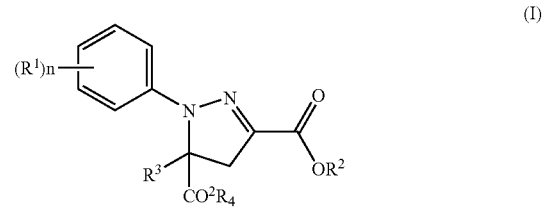

(I)

in which
$(R^1)_n$ is n radicals $R^1$ where the $R^1$ are identical or different and are each halogen or $(C_1-C_4)$-haloalkyl,
n is an integer from 1 to 3,
$R^2$ is hydrogen, $(C_1-C_6)$-alkyl, $(C_1-C_4)$-alkoxy-$(C_1-C_4)$-alkyl, $(C_3-C_6)$-cycloalkyl, tri-$(C_1-C_4)$-alkyl-silyl or tri-$(C_1-C_4)$-alkyl-silylmethyl,
$R^3$ is hydrogen, $(C_1-C_6)$-alkyl, $(C_1-C_6)$-haloalkyl, $(C_2-C_6)$-alkenyl, $(C_2-C_6)$-alkynyl or $(C_3-C_6)$-cycloalkyl, and
$R^4$ is hydrogen or $(C_1-C_{12})$-alkyl.

2. A herbicide-safener combination as claimed in claim 1 wherein component (A) is:
   clethodim (A4), cycloxydim (A5) or tepraloxydim (A7) or salts thereof.

3. A herbicide-safener combination as claimed in claim 1 wherein
$(R^1)_n$ is n radicals $R^1$ where the $R^1$ are identical or different and are each F, Cl, Br or $CF_3$,
n is 2 or 3,
$R^2$ is hydrogen or $(C_1-C_4)$-alkyl,
$R^3$ is hydrogen, $(C_1-C_4)$-alkyl, $(C_2-C_4)$-alkenyl or $(C_2-C_4)$-alkynyl, and
$R^4$ is hydrogen or $(C_1-C_8)$-alkyl.

4. A herbicide-safener combination as claimed in claim 1, wherein component (B) is, ethyl 1-(2,4-dichlorophenyl)-5-(ethoxycarbonyl)-5-methyl-2-pyrazoline-3-carboxylate.

5. A herbicide-safener combination as claimed in claim 4, wherein component (A) is clethodim (A4) or a salt thereof.

6. A herbicide-safener combination as claimed in claim 4, wherein component (A) is cycloxydim (A5) or a salt thereof.

7. A herbicide-safener combination as claimed in claim 4, wherein component (A) is tepraloxydim (A7) or a salt thereof.

8. A herbicide-safener combination as claimed in claim 1, wherein the active compounds (A) and (B) are present in a weight ratio of from 200:1 to 1:200.

9. A herbicidal composition which comprises a herbicide-safener combination as defined in claim 1 and additionally contains formulation auxiliaries.

10. A method for protecting crop plants against phytotoxic side-effects of a herbicide (A), which comprises application of an antidotally effective amount of one or more safeners (B) before, after or simultaneous with the application of herbicide (A) to the plants, parts of plants, plant seeds or the area under cultivation, herbicide (A) and safener (B) being defined as in claim 1.

11. A method as claimed in claim 10, wherein component (B) is, ethyl 1-(2,4-dichlorophenyl)-5-(ethoxycarbonyl)-5-methyl-2-pyrazoline-3-carboxylate.

12. A method as claimed in claim 11, wherein component (A) is clethodim (A4) or a salt thereof.

13. A method as claimed in claim 11, wherein component (A) is cycloxydim (A5) or a salt thereof.

14. A method as claimed in claim 11, wherein component (A) is tepraloxydim (A7) or a salt thereof.

15. A method for selectively controlling weeds in crops of useful plants which comprises application of a herbicide-safener combination as claimed in claim 1 to the plants wherein compounds (A) and (B) are applied simultaneously, separately or sequentially.

16. A method as claimed in claim 15, wherein component (B) is, ethyl 1-(2,4-dichlorophenyl)-5-(ethoxycarbonyl)-5-methyl-2-pyrazoline-3-carboxylate.

17. A method as claimed in claim 16, wherein component (A) is clethodim (A4) or a salt thereof.

18. A method as claimed in claim 16, wherein component (A) is cycloxydim (A5) or a salt thereof.

19. A method as claimed in claim 16, wherein component (A) is tepraloxydim (A7) or a salt thereof.

* * * * *